United States Patent [19]

Green

[11] Patent Number: 5,110,600
[45] Date of Patent: May 5, 1992

[54] METHOD OF TREATING VIRAL INFECTIONS WITH AMINO ACID ANALOGS

[75] Inventor: Melvin H. Green, San Digeo, Calif.

[73] Assignee: The Regents of the University of California, Oakland, Calif.

[21] Appl. No.: 148,069

[22] Filed: Jan. 25, 1988

[51] Int. Cl.⁵ .................................. A61K 9/127
[52] U.S. Cl. ....................... 424/45 D; 424/422; 514/2; 514/885
[58] Field of Search .............. 424/45 D, 422, 439; 514/885, 2

[56] References Cited

U.S. PATENT DOCUMENTS

| | | | |
|---|---|---|---|
| 3,804,776 | 4/1974 | Yazawa et al. | 424/450 X |
| 4,185,090 | 1/1980 | McIntire | 514/885 X |
| 4,338,335 | 7/1982 | McAleer et al. | 435/235 X |
| 4,377,567 | 3/1982 | Geho | 424/450 X |
| 4,400,295 | 8/1983 | Odtsu et al. | 424/63 X |
| 4,638,045 | 1/1987 | Kohn et al. | 424/78 X |
| 4,713,244 | 12/1987 | Bawa et al. | 424/486 X |
| 4,717,716 | 1/1988 | Nagai et al. | 514/885 X |
| 4,744,989 | 5/1988 | Payne et al. | 424/491 X |
| 4,752,425 | 6/1988 | Martin et al. | 424/450 X |
| 4,755,388 | 7/1988 | Heath et al. | 424/450 |
| 4,761,288 | 8/1988 | Mezei | 424/450 |
| 4,774,320 | 9/1988 | Tagliabue et al. | 514/885 X |
| 4,795,739 | 1/1989 | Lifson et al. | 514/8 |
| 4,855,090 | 8/1989 | Wallach | 514/885 X |
| 4,871,488 | 10/1989 | Mannino et al. | 514/885 X |
| 4,883,661 | 11/1989 | Daly et al. | 514/885 X |

FOREIGN PATENT DOCUMENTS 3230151 2/1984 Fed. Rep. of Germany ...... 514/885

OTHER PUBLICATIONS

Mitsuya et al., "Strategies for antiviral therapy in AIDS" *Nature*, 325:773-778 (1987).
G. A. Rosenthal, "The biological effects and mode of action of L-Canavanine, a structural analogue of L-Arginine", *Qt. Rev. Biol.*, 52:155-178 (1977).
Cummings et al., "Structural aberations in T-even bacteriophage. ill. induction of lollipops and their partial characterization", *Virology* 54:245-261 (1973).
Schachtele et al., "Canavanine death in *Escherichia coli*", *J. Mol. Biol.*, 14:474-489 (1965).
Neurath et al., "Inhibition of adenovirus replication by Canavanine", *Biochem. Biophys. Res. Commun.*, 41: 1509-1517 (1970).
McMahon et al., "The effects of Canavanine and arginine starvation on macromolecular synthesis in *Chlamydomonas reinhardi*", *J. Gen. Microbiol.*, 73:239-250 (1972).
Kruse et al., "Incorporation of Canavanine into protein of Walker carcinosarcoma 256 cells cultured in Vitro", *Cancer Res.*, 19:122-125 (1959).
Dahlman et al., "Further studies of the effect of L-Canavanine on the tobacco hornworm, *Manduca sexta*", *J. Insect Physiol.*, 22:265-271 (1976).
D. Bell, "The effect of Canavanine on herpes simplex virus replication", *J. Gen. Virol.*, 22:319-330 (1974).
W. F. Prouty, "Degradation of abnormal proteins in HeLa cells", *J. Cell Physiol.*, 88:371-382 (1976).
Goldberg et al., "Intercellular protein degradation in mammalian and bacterial cells: part 2", *Ann. Rev. Biochem.*, 45:747-803 (1976).
Green et al., "Antitumor activity of L-Canavanine against L1210 Murine leukemia", *Cancer Research* 40:535:537 (1980).
Berjis et al., "Selective cytotoxicity of L-Canavanine in tumorigenic Madin-Darby canine kidney T₁ cells", *Interactions*, 60:305-315 (1986).
Thomas et al., "Growth inhibition of a rat colon tumor by L-Canavanine", *Cancer Research*, 46:2898-2903 (1986).

(List continued on next page.)

Primary Examiner—Thurman Page
Attorney, Agent, or Firm—SaraLynn Mandel

[57] ABSTRACT

Retrovirally-infected cells are selectively killed as compared with uninfected cells using an effective amount of amino acid analogs of naturally occurring amino acids, such as L-canavanine (an analog of arginine).

15 Claims, 8 Drawing Sheets

OTHER PUBLICATIONS

Malinow et al., "Systemic lupus erythematosus-like syndrome in monkeys fed alfalfa sprouts: role of a nonprotein amino acid", *Science*, 216:415-417 (1982).

B. D. Noe, "Inhibition of islet prohormone to hormone conversion by incorporation of arginine and lysine analogs", *J. Biol. Chem.*, 250:7623-7630 (1975).

Christner et al., "Inhibition of the assembly and secretion of procollagen by incorporation of a Thereonine analogue, Hydroxynorvaline", *J. Biol. Chem.*, 250:7623-7630 (1975).

Green et al., "Enhancement of human tumor cell killing by L-Canavanine in combination with γ-radiation", *Cancer Res.*, 43:4180-4182 (1983).

Thomas et al., "Toxicity and pharmacokinetics of the nonprotein amino acid L-Canavanine in the rat", *Toxicology and Applied Pharmacology*, 91:395-405 (1987).

Yarchoan et al., "Development of antiretroviral therapy for the acquired immunodeficiency syndrome and related disorders", *New England J. of Med.*, 316(9):557-563 (1987).

Kaplan et al., "Treatment of patients with acquired immunodeficiency syndrome and associated manifestations", *JAMA*, 257(10): 1367-1374 (1987).

Naha et al., "Reappraisal of L-Canavanine as an anti-tumor agent", *Cell Biology Internatl. Rpts.*, 4(2) 155-165 (1980).

METHOD OF TREATING VIRAL INFECTIONS WITH AMINO ACID ANALOGS

FIELD OF THE INVENTION

This invention relates to the use of amino acid analogs to treat diseases caused by virus infected cells. More particularly, the invention concerns the use of L-canavanine, an amino acid analog of arginine, to selectively kill cells infected with a retrovirus and to inhibit the production of infectious retroviruses.

BACKGROUND OF THE INVENTION

There is a recognized need for antiviral agents to combat the threat to millions of humans from refractory viruses such as the retrovirus believed to cause Acquired Immunodeficiency Syndrome ("AIDS") disease.

Currently AIDS disease is killing thousands of humans throughout the world, and wreaking psychological havoc in its wake. AIDS is caused by a retrovirus, human T4 lymphotropic virus (HTLV-III), more recently designated as human immunodeficiency virus or "HIV". This virus has the capacity to replicate within the cells of the human immune system to the destruction of helper/inducer (T4+ or CD4+) T cells. Retroviruses are a type of virus that replicates through a DNA intermediate, i.e. during replication genetic information is transferred from RNA to DNA, in a reverse or "retro" direction. This step is catalyzed by reverse transcriptase, a viral DNA polymerase. Many retroviruses are capable of inducing neoplastic transformation in infected target cells, although HIV is an exception to this rule. AIDS disease manifests as a loss of delayed-type cutaneous hypersensitivity reactions, a loss of certain in vitro T-cell proliferative responses, excessive immunoglobulin production by B cells, and a loss of in vitro cytotoxic T-cell responses.

Although the immunodeficiency state of AIDS disease is generally progressive and fatal, the effect of infection with HIV varies. While AIDS disease results in a severe suppression of the immune system manifesting a number of "opportunistic" infections (e.g. caused by microorganisims that rarely cause disease in individuals with normal immune systems) and cancers, some individuals infected with HIV may not develop AIDS disease. AIDS-related complex (ARC) is a condition characterized by fevers, diarrhea and swollen lymph nodes in approximately 50% of individuals infected with HIV. In both AIDS and ARC, the HIV may be present in cells for prolonged periods of time (months and even years) without causing cell death.

Although considerable effort and expense is being devoted to developing an effective treatment for AIDS, the disease has failed to respond significantly to existing therapies. Therapeutic intervention for the treatment of pathogenic human retroviruses such as AIDS has typically targeted different stages in the life cycle of the HIV virus for administration of antiviral agents. A certain amount of success has been met by attempts to prevent viral replication, for example using reverse transcriptase inhibitors such as the 2'3'-dideoxy-nucleoside analog 3'-azido 3'-deoxythymidine (AZT). Other approaches include the use of antibodies to the virus or cell receptor, drugs that block virus fusion with a target cell or interfere with viral uncoating; inhibitors of RNase H activity and interferons. The testing of antiretroviral agents has used in vitro screening systems to determine whether the agent can inhibit the replication and T-cell killing activity of the virus (Mitsuya et al. *Nature*, 325:773-778 (1987)).

L-canavanine is an amino acid found in the Lotoidae, a major subfamily of the Leguminosae, and it is the principal free amino acid of numerous legumes (Rosenthal, *Qt. Rev. Biol.*, 52:155-178 (1977)). It is a guanidinooxy analog of the amino acid L-Arginine, having the formula $H_2N-C(=NH)-NH-O-CH_2-CH_2-CH(NH_2)COOH$. The guanidinooxy group of canavanine has a pK of 8.2 as compared to a pK of 10.8 for the guanidino group of arginine. This decreased basicity may effect the activity and structural properties of proteins containing canavanine as demonstrated by the appearance of T4 phage possessing giant polyheads as a result of the incorporation of canavanine (Chapman et al., *Virology* 54:245-261 (1973)).

The antimetabolic properties of canavanine have been observed in vitro in many types of microorganisms, plants, insects and animal cells and appear to be due to a marked inhibition of RNA and DNA synthesis, with little effect on net protein synthesis. The inhibitory effects are readily reversible or prevented by the administration of arginine (Id.). Although the mechanism is uncertain, the basis of toxicity is believed to stem from the incorporation of canavanine into proteins, as has been demonstrated in several organisms including *Escherichia coli* (Schachtele et al., *J. Mol. Biol.*, 14:474-489 (1965); adenovirus (Neurath et al., *Biochem. Biophys. Res. Commun.*, 41:1509-1517 (1970); *Chlamydomonas reinhardi* (McMahon et al., *J. Gen. Microbiol.* 73:239-250 (1972)); Walker carcinosarcoma 256 cells (Kruse et al., *Cancer Res,* 19:122-125 (1959)) and tobacco hornworm larvae (Cahlman et al, *J. Insect Physiol.*, 22:265-271 (1976)). L-canavanine is also known to inhibit cellular and viral replication rapidly (Bell, *J. Gen. Virol.*, 22:319-330 (1974)) and to promote more rapid degradation of proteins which have been structurally modified as a result of its incorporation (Prouty, *J. Cell Physiol.*, 88:371-382 (1976) and Goldberg et al., part 2, *Ann. Rev. Biochem.* 45:747-803 (1976)).

Green et al. (*Cancer Research* 40:535-537 (1980)) demonstrated that L-canavanine possesses antitumor activity in leukemic mice. L-canavanine was found to selectively inhibit DNA synthesis by L1210 leukemic cells as determined from ascites fluid, and to significantly prolong the lifespan of mice bearing these cells. These results indicate that L-canavanine selectively kills L1210 leukemic cells in mice.

Subsequently, L-canavanine was shown to exhibit selective cytotoxicity on chemically transformed derivatives of normal Madin-Darby canine kidney (MDCK) epithelial cells (Berjis et al., *Interactions*, 60:305-315 (1986)). Under conditions where the canavanine reversibly arrested growth of the normal MDCK cells, more than 90% of the tumorigenic MDCK-T cells were killed. The selective toxicity was not due to any difference in growth rates of the two cell types or from inhibition of protein synthesis or DNA replication.

Recently, the inhibitory effects of L-canavanine on the growth of a solid animal tumor in vivo have been reported (Thomas et al., *Cancer Research* 46:2898-2903 (1986)). Reduction in tumor volume of rat colon tumor was observed in animals receiving 2 g/kg of L-canavanine for five days. Cumulative toxicity caused death in some of the animals at higher doses (3 g/kg for 9 days).

The toxicity of L-canavanine in mammals was explored by prolonged oral feeding of monkeys with the analog which resulted in the induction of biochemical effects characteristic of the autoimmune disease, systemic lupus erythematosus (Malinow et al., *Science*, 216:415-417 (1982)).

The present invention provides a method of using the amino acid analog L-canavanine to selectively kill mammalian cells infected with and producing virus and to treat disease caused by the virus.

SUMMARY OF THE INVENTION

The present invention provides a method for treating viral infection in a mammal in need of such treatment comprising administering to the mammal an effective dose of a pharmaceutical preparation containing an analog of a naturally occurring amino acid capable of being incorporated into newly synthesized proteins for killing cells infected with a virus. The method for treating viral infection in a mammal in need of such treatment also comprises administering to the mammal an effective dose of a pharmaceutical preparation containing L-canavanine sufficient to kill cells infected with virus in a pharmaceutically acceptable carrier. The infection may be by retroviruses that infect humans, such as Human Immunodeficiency Virus (HIV), or by retroviruses that infect other mammals, for example Feline Leukemia Virus that infects cats. The effective dose of L-canavanine is preferably sufficient to provide a molar ratio of L-canavanine to arginine in the mammal's blood serum of from 1:1 to 10:1 L-canavanine to arginine. The method may also consist of co-administering a chemotherapeutic agent capable of inhibiting viral replication.

The invention also provides a method for selectively killing virally-infected cells and inhibiting viral replication in a mixed population of virus-infected cells and uninfected cells in medium, by contacting said mixed population of cells with an effective amount of L-canavanine.

DETAILED DESCRIPTION OF THE INVENTION

L-canavanine is the preferred amino acid analog for use in the method of this invention to treat retroviral infection. However, other natural and synthetic amino acid analogs capable of incorporation into proteins synthesized by mammalian cells, but that do not inhibit protein synthesis, may be used. These analogs include less basic analogs of basic amino acids including arginine, lysine and histidine. (Noe, *J. Biol. Chem.* 265:4940-4946 (1981) and Christner et al., *J. Biol. Chem.* 250:7623-7630 (1975)).

L-canavanine was found to demonstrate selective cytotoxicity in vitro against cells infected by a mammalian retrovirus. This analog was further found to selectively kill HIV-infected human cells in culture with minimal cytocidal effect on uninfected control cells. These effects are described in the following, nonlimiting Examples.

EXAMPLE I

Toxicity of Retrovirus-Producing Cells to L-Canavanine

Four immortalized mouse lymphoma cell lines were obtained (Dr. S. Baird, Univ. of California, San Diego, and Veterans Administration Hospital, San Diego, Calif.) from mice previously infected by the retrovirus murine leukemia virus ("MuLV"). The cells lines were designated: 307; 315T; W22 and WR123. All four cell lines produce MuLV antigens which are detectable on the cell surface. However only line 307 is known to produce infectious MuLV virus particles ("virions"). The four cell lines grow at similar rates in culture.

All four cell lines were grown in Dulbecco's Modified Eagle's (DME) high glucose medium supplemented with 10% Fetal Calf Serum (FCS) at 37° C. in a humidified atmosphere containing 10% $CO_2$. 1 ml of cells were grown per well in microtiter dishes. Three separate wells were tested for each assay of cell viability.

A stock solution of L-canavanine (Calbiochem, La Jolla, Calif.) was prepared and stored at −5° C. after neutralization to pH 7 and filter sterilization. Serial dilutions of the stock solution were added to each well of the cell cultures at day 0 at doses ranging from 1X to 5X, where X was the concentration of arginine in the medium (84 μg/ml.)

Cell viability was assessed using the trypan blue exclusion assay by counting total cells and viable cells by hemacytometer counts after staining with trypan blue.

Figure 1:
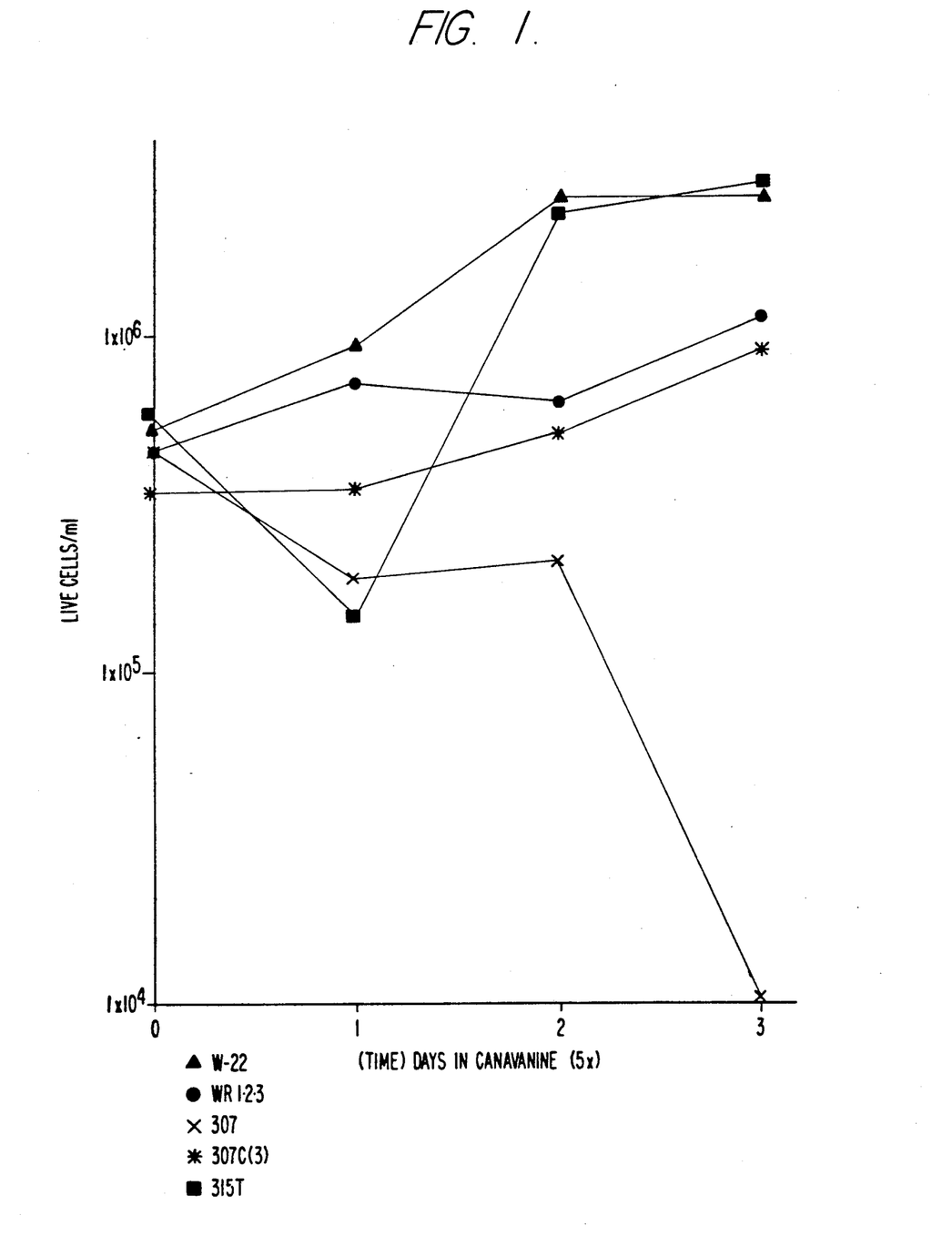
FIG. 1 is a graph showing the results of murine lymphoma cell viability after treatment with L-canavanine as described in Example I, infra.

The results are depicted in FIG. 1 which is a graph indicating the number of viable cells per ml as a function of time after exposure to L-canavanine for the five different cell lines. The 5X dose was selected after preliminary experiments indicating that maximal differential cell kill occurred with that dose. Cell line 307C(3) is a canavanine resistant line that was derived from line 307 by passaging the cells after three successive treatments with L-canavanine. As can be seen from the graph, after two days of treatment with L-canavanine, a dramatic reduction in viability occurred for cells of line 307 as compared to the other lymphoma cell lines, demonstrating a strong sensitivity of this cell line to L-canavanine. Cell line 307 was the only one of the four original cell lines (307, 315T, W22 and WR123) continually producing infectious retroviruses in culture.

Figure 2:
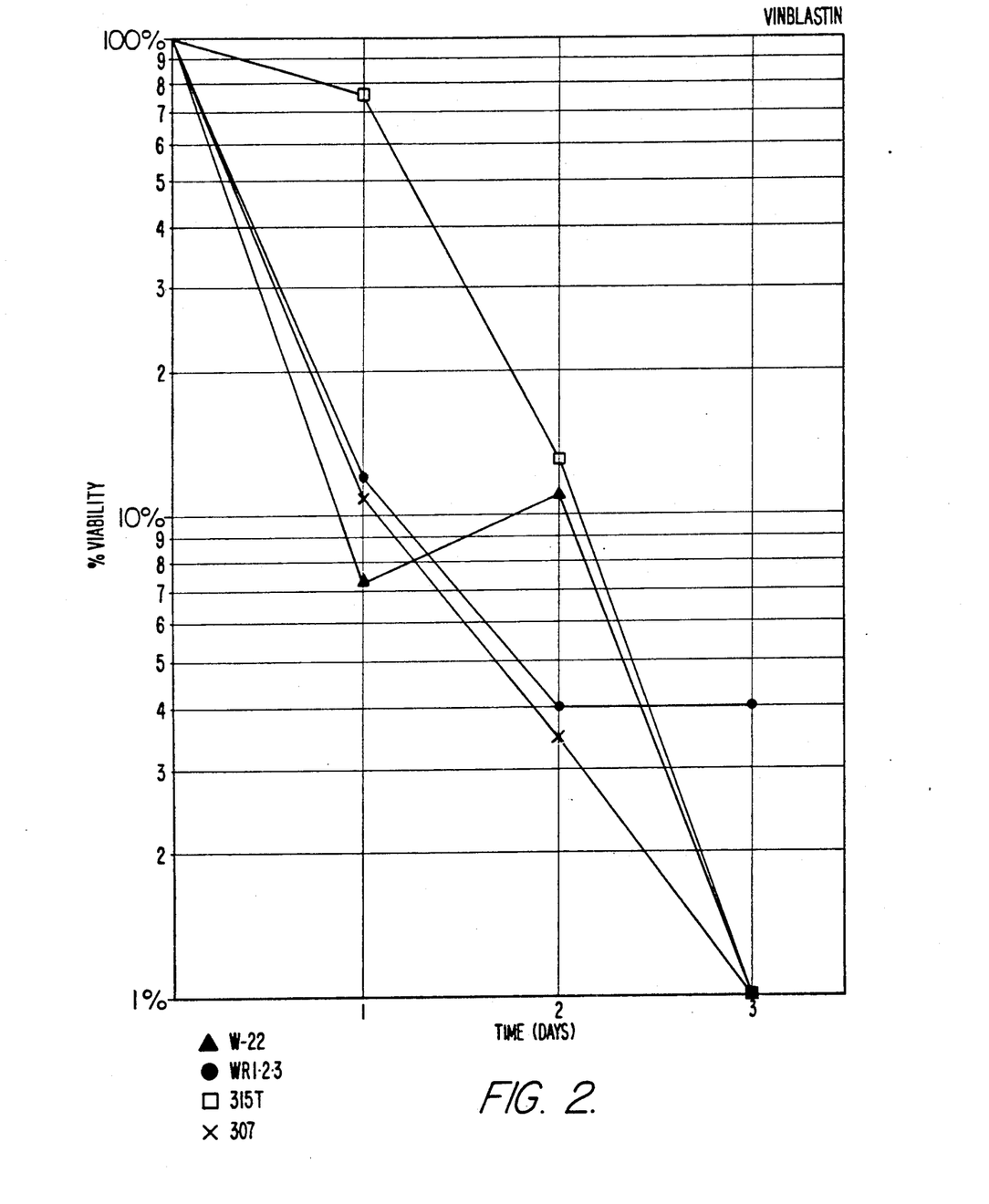
FIG. 2 is a graph showing the results of murine lymphoma cell viability after treatment with the drug vinblastine, as described in Example I, infra.
Figure 3:
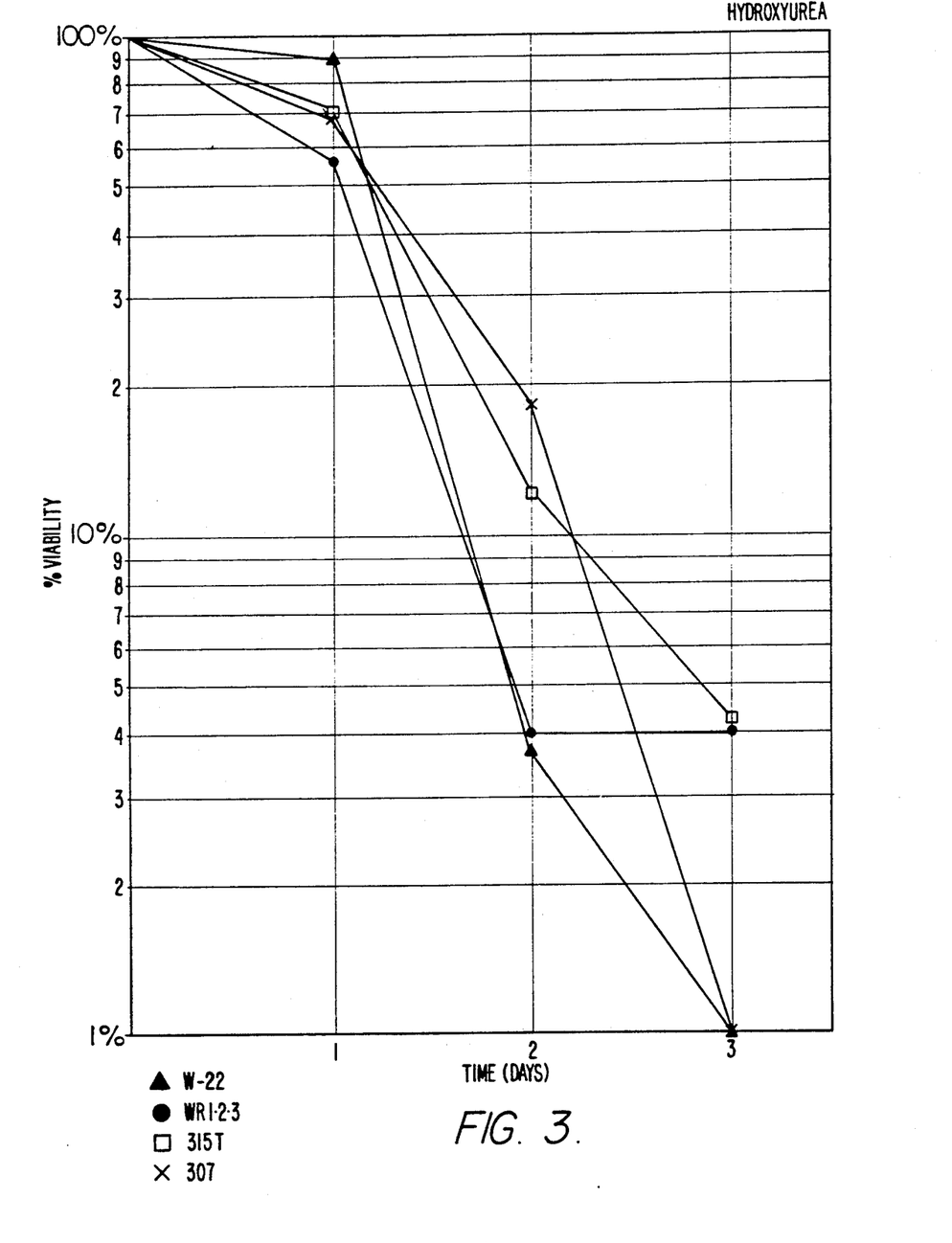
FIG. 3 is a graph showing the results of murine lymphoma cell viability after treatment with the drug hydroxyurea, as described in Example I, infra.
Figure 4:
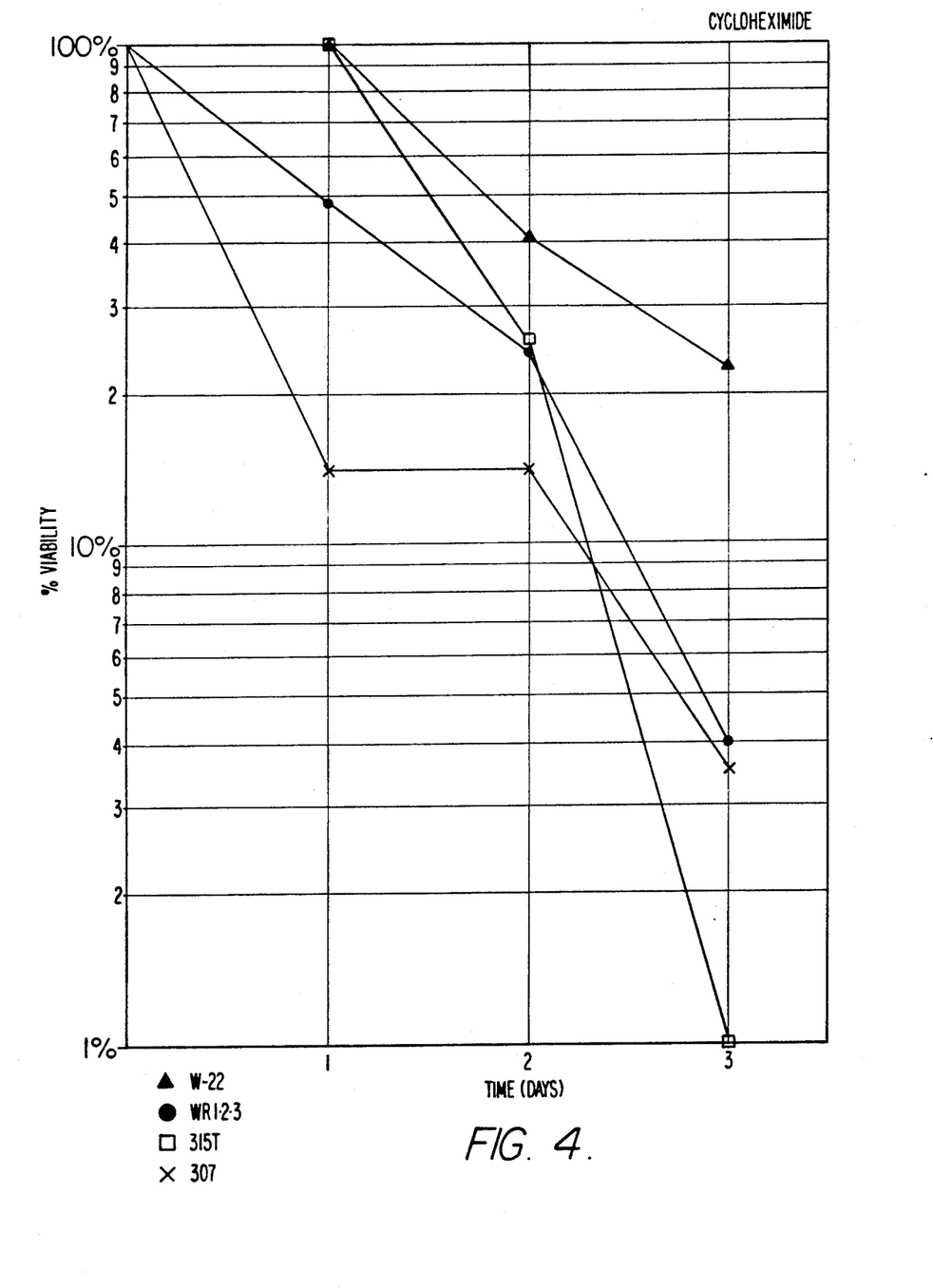
FIG. 4 is a graph showing the results of murine lymphoma cell viability after treatment with the drug cycloheximide, as described in Example I, infra.

The sensitivity of cell line 307 to L-canavanine was not a general drug sensitivity of this line. In a subsequent experiment the four cell lines were exposed to vinblastine, hydroxyurea, and cycloheximide and all four lines had similar sensitivities to these drugs as depicted in FIGS. 2–4.

These results suggest that L-canavanine is capable of exhibiting selective cytotoxicity against cells actively producing retroviruses.

EXAMPLE II

Effect of L-Canavanine on HIV-Infected Human Cells in Culture

Logarithmetically growing human T-lymphoid cells (line CEM) cell line permissive for HIV replication with moderate cytopathic effect (Dr. David Pauza, Salk Institute La Jolla, Calif.) were infected at a multiplicity of 0.2 TID /cell. The infected and uninfected populations were cultured at $5 \times 10^3$ cells/ml in DME medium plus 10% heat inactivated FCS. L-canavanine (Calbiochem, La Jolla, CA) was added directly to this medium at a mass ratio with arginine of 0 to 10. The original arginine content of the medium was 84 µg/ml. Aliquots were removed on days 0, 1, 2 and 3 for uninfected cells and on days 0 and 3 for infected cells. Cell viability was determined by measuring $^3$H-thymidine uptake using standard methods as described by Green et al., 1980, supra. Cell viability was also determined using the trypan blue exclusion assay as in Example I.

Figure 5:
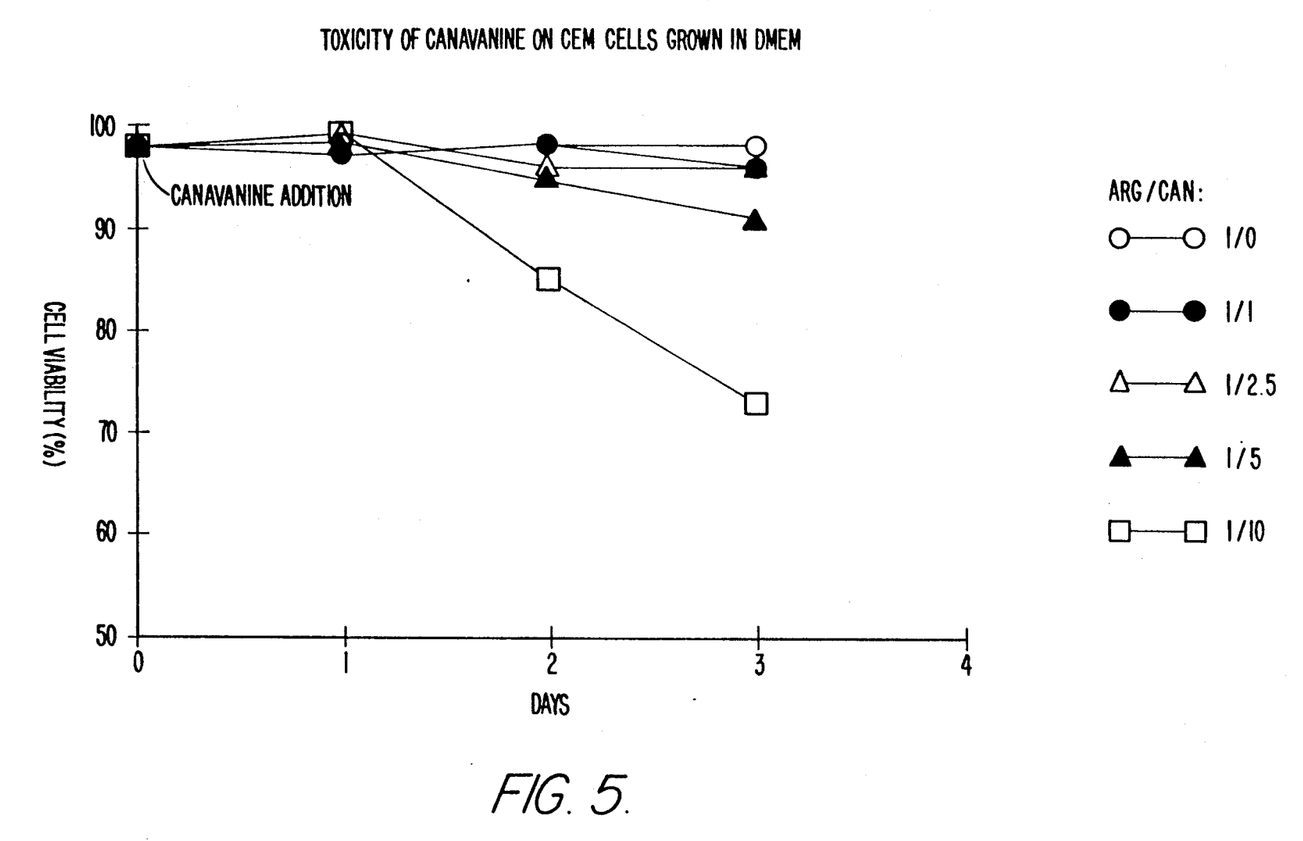
FIG. 5 is a graph showing the effects of L-canavanine on the viability of non-infected human lymphoid cells (line CEM) as described in Example II, infra.
Figure 6:
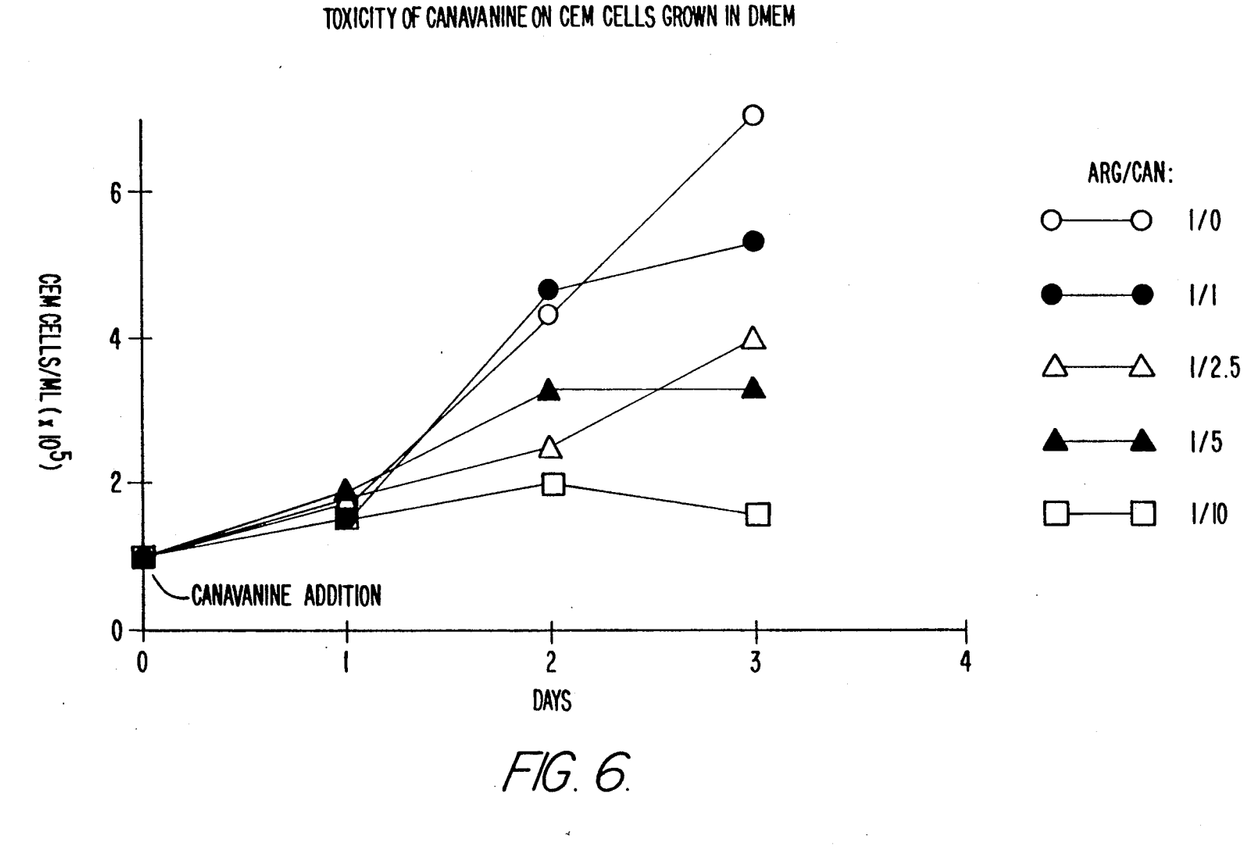
FIG. 6 is a graph showing the effects of L-canavanine on the growth of CEM cells as described in Example II, infra.

The effect of L-canavanine on the growth and viability of CEM cells infected and uninfected with HIV virus is shown in FIGS. 5 and 6. At doses of arginine to L-canavanine of 1:2.5 (L-canavanine dose of 2.5X where X was the concentration of arginine in the medium) for 3 days, uninfected CEM cells remained viable (greater than 90%) (FIG. 5) and showed greater than 50% of the growth of control cultures (FIG. 6). At the highest dose (10X) the cell numbers remained nearly constant over the three day period (FIG. 6), and more than 70% of the cells remained viable (FIG. 5). Less than 10% of the CEM cells were killed at doses of L-canavanine ranging from 1X to 5X and considerable cell growth occurred during this period (FIGS. 5 and 6).

In contrast, using the trypan blue dye exclusion assay, less than 5% of the HIV-infected CEM cells treated at L-canavanine doses of 1, 2.5, 5 and 10X were viable three days post-treatment. Infected controls (without canavanine treatment) exhibited greater than 90% viability at this time.

Figure 7:
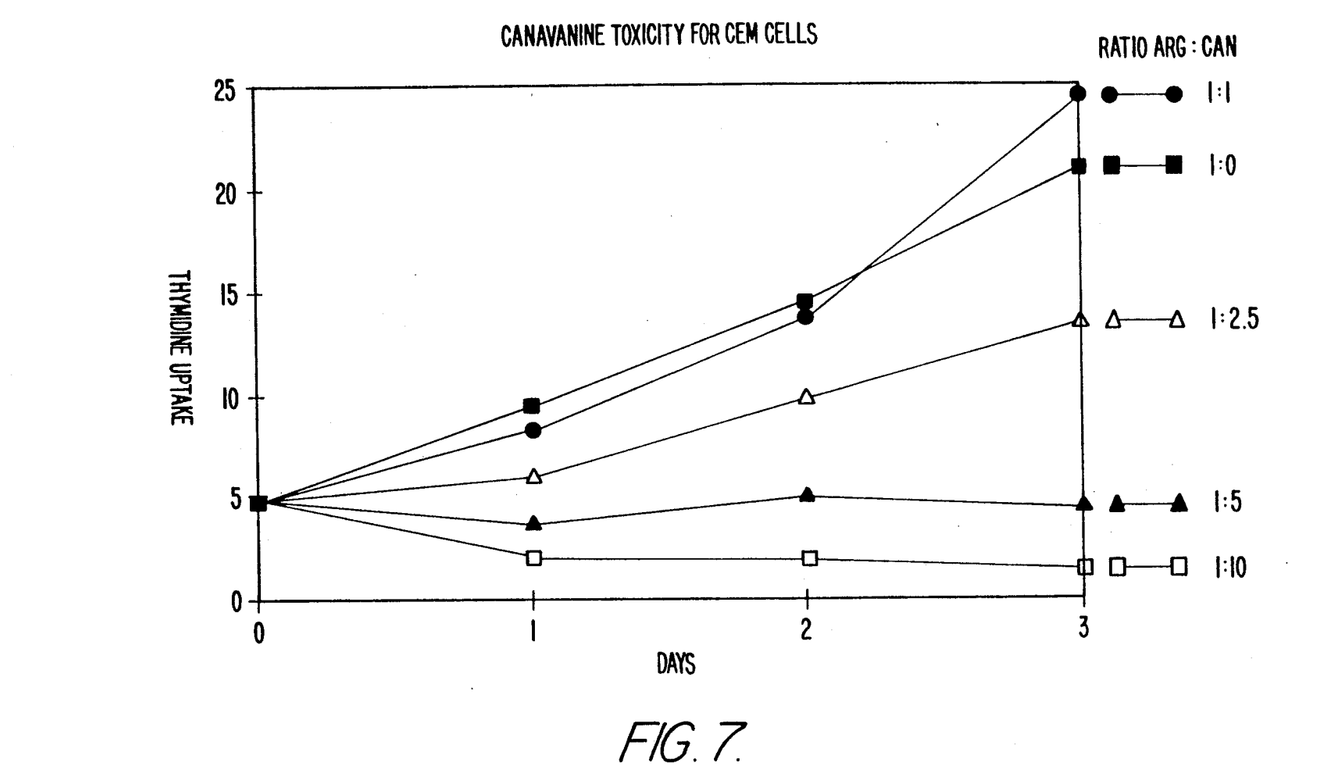
FIG. 7 is a graph depicting the effect of L-canavanine on CEM cell viability as determined by thymidine uptake as described in Example II, infra.
Figure 8:
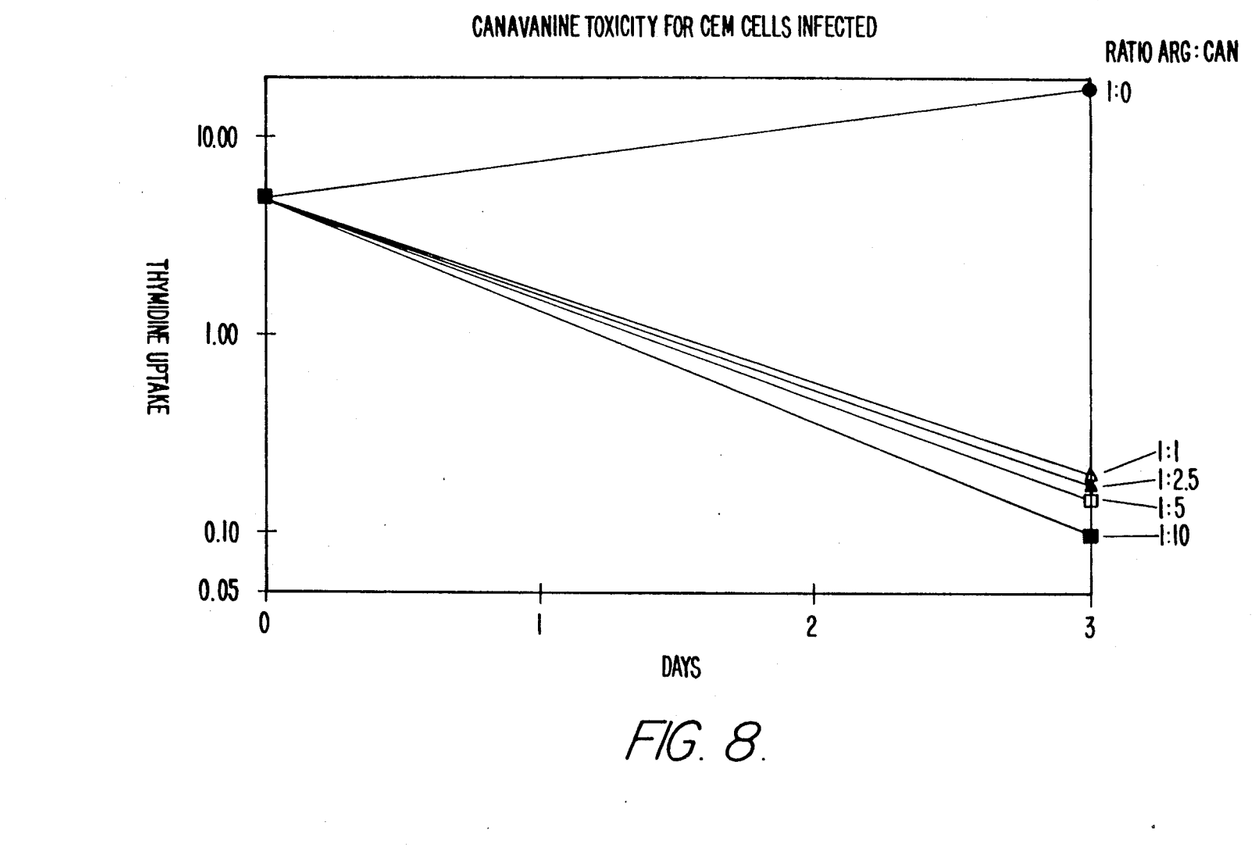
FIG. 8 is a graph showing the effect of L-canavanine on thymidine uptake of CEM cells infected with the HIV virus.

These results are confirmed by determination of the effects of canavanine on DNA synthesis using $^3$H-thymidine uptake assays. Uninfected CEM cells showed little inhibition or increase of DNA synthesis at canavanine doses of 5X and 10X (FIG. 7). This indicates that minimal cell kill or growth took place during the three-day period of canavanine treatment. At doses of 1X and 2.5X, DNA synthesis increased in relation to increases in cell number. In striking contrast, there was more than 95% inhibition of DNA synthesis at every dose of canavanine in the infected CEM cells at day three (FIG. 8). These results correlate well with the observation that less than 5% of the original number of HIV-infected cells remained viable at this point.

These results demonstrate that HIV-infected CEM cells are considerably more sensitive in vitro to treatment with L-canavanine than are uninfected control cells. Preferential killing of viral-infected cells by less basic amino acid analogs such as L-canavanine provides a new approach to the treatment of retroviral diseases such as AIDS and diseases caused by HTLV I, II, IV and V and Feline Leukemia Virus (FeLV). Amino acid analogs may also be effective in killing cells infected with a variety of DNA viruses, for example Herpes Simplex Virus (HSV).

Because L-canavanine has been determined not to be mutagenic (Ames, *Science* 204:587 (1979)), it is also likely that it is not carcinogenic. Moreover, the toxic effects of the analog may be quickly reversed by administering the natural amino acid arginine over a suitable period of time. (Green et al., *Cancer Res.* 43:4180–4182 (1983)).

Since L-canavanine has been demonstrated to kill tumor cells in live animals (Green et al., 1980, supra and Thomas et al., supra) and as demonstrated herein, can selectively kill retrovirally infected human cells in vitro, it shows promise for treatment of retrovirally infected cells in vivo in humans as well as animals suffering from viral diseases. Treatment with the analogs will irreversibly halt viral production in infected cells as a result of cell death. Because the amino acid analogs such as L-canavanine will be incorporated into newly synthesized cellular and viral proteins, the present method should further result in lowered subsequent cell infection by the newly synthesized virus because of altered structure and lowered numbers of the viruses. The fact that L-canavanine has been found to be tolerable when administered orally in primates (Malinkow, supra) suggests that humans may tolerate the drug when administered in an appropriate form and dosage.

L-canavanine as well as other natural and synthetic amino acid analogs that are readily incorporated into newly synthesized proteins, may be used to treat retroviral disease in a mammal by administration of effective amounts of the pharmaceutical preparations containing the analogs. In this respect, it is important to note that the relative ratios of L-canavanine to arginine appeared significant in the in vitro cell toxicity studies described herein. These ratios may determine the amount of canavanine relative to arginine that is incorporated into proteins. Therefore, in determining the appropriate dosage for an individual subject the amount of arginine present in the blood of the subject must be measured and the ratio of L-canavanine to arginine optimized. Based on the in vitro results described herein, ratios in the range of from 1:1 to 10:1 L-canavanine to arginine are preferable. Appropriate dosages will also depend on the body weight of the mammal and stage and severity of infection.

For initial treatment it may be necessary to maintain relatively high and constant levels of the L-canavanine in the mammal's body to obtain maximum kill of the virally infected cells. In addition, since the virus produced by the infected cells may itself be killed as a result of L-canavanine incorporation during viral replication, the continued presence of L-canavanine may be necessary to control the spread of the virus. Therefore, continuous infusion of the amino acid analog or frequent injections or other form of sustained release of the analog may be warranted. Because the half-life of L-canavanine in the blood of mice has been determined to be relatively short (Green et al., 1980, supra) the frequency and amount of L-canavanine to be administered should be calculated so as to attain a sufficient level of L-canavanine to achieve optimal selective cell kill for virally infected cells in vivo. This calculation should also take into account the amount of arginine present in the blood serum of a subject to achieve the desired ratios of arginine to L-canavanine described above, in vivo. The exact regimen for administration of the analogs disclosed herein will necessarily be dependent upon the needs of the individual subject being treated, the type of treatment and, of course, the judgment of the attending practitioner.

The analogs may be administered in association with a pharmaceutically acceptable carrier. The text *Remington's Pharmaceutical Sciences*, 15th Ed. by E. W. Martin (Mark Publ. Co., 1975) discloses typical carriers and methods of preparation, which disclosure is incorporated herein by reference. The pharmaceutical amino acid analog preparations may be administered orally, parenterally (e.g. intravenously (i.v.), intra muscularly, or intraperitoneal (i.p.) or the like depending on the nature of the viral infection being treated and at dose levels appropriate for the body weight of the mammal. In addition, the preparations may be applied topically to treat viral infections of exposed tissues such as the skin and eyes or mouth, for example by HSV and other viruses for which L-canavanine has been demonstrated to be effective. Since the compounds are amino acids, it is also possible to incorporate the analogs into normal food products for oral intake.

In addition to the use of L-canavanine, effective retroviral therapy may be accomplished by combining administration of amino acid analogs such as L-canavanine with other chemotherapeutic or antiviral agents that act by other mechanisms directed against retroviruses. For example, the analogs may be administered along with drugs such as interferons or base analogs such as AZT, and antibodies to the virus or to cellular receptors for the virus, to retard viral replication as well as to kill virally infected cells. In addition, virally infected cells may be targeted in vivo for treatment with the amino acid analogs using targeting agents. For example, the analogs may be encapsulated within liposomes that selectively interact with the virally infected cells. Furthermore, such targeting agents may be associated with an additional chemotherapeutic agent and then administered along with or complexed to the amino acid analogs for enhanced treatment of a viral infection.

The foregoing examples have been presented to illustrate the present invention and are not to be construed as limitations on the invention's scope which is instead defined by the following claims.

What is claimed is:

1. A method for treating viral infection in a mammal in need of such treatment comprising administering to said mammal an effective dose of a pharmaceutical preparation containing L-canavanine in an amount sufficient to provide a molar ratio of said L-canavanine to arginine of from 1:1 to 10:1 to selectively kill cells infected with virus.

2. The method of claim 1 wherein said mammal is a human and the virus is a retrovirus.

3. The method of claim 1 wherein said mammal is human and the virus is Human Immunodeficiency Virus.

4. The method of claim 1 wherein said mammal is feline and the virus is the retrovirus Feline Leukemia Virus.

5. The method of claim 1 wherein said virus is Herpes Simplex Virus.

6. The method of claim 1 wherein said administration is selected from the group consisting of intravenous, intraperitoneal, intramuscular and subcutaneous.

7. The method of claim 1 wherein said administration is oral.

8. The method of claim 1 wherein said administration is by continuous infusion.

9. A method for selectively killing virally-infected cells and inhibiting viral replication in a mixed population of virus-infected cells and uninfected cells in a medium, comprising contacting said mixed population of cells with an effective amount of L-canavanine sufficient to provide a molar ratio of L-canavanine to arginine in the medium of from 1:1 to 10:1.

10. The method of claim 9 wherein said mixed population of cells is human cells.

11. The method of claim 10 wherein said infected cells are infected with Human Immunodeficiency Virus.

12. The method of claim 1 further comprising co-administering a chemotherapeutic agent capable of inhibiting viral replication.

13. The method of claim 12 wherein said chemotherapeutic agent is interferon.

14. The method of claim 1 wherein said L-canavanine is encapsulated by liposomes that selectively interact with said cells infected with a virus.

15. A method for treating viral infection in a mammal in need of such treatment comprising administering to said mammal in a pharmaceutically acceptable carrier an effective dose of a pharmaceutical preparation containing an analog of an amino acid selected from the group consisting of arginine, lysine and histidine in an amount sufficient to selectively kill cells infected with virus.

* * * * *